United States Patent [19]

Uchiyama et al.

[11] 3,962,207

[45] June 8, 1976

[54] METHOD OF PRODUCING α-L-ASPARTYL-L-PHENYLALANINE LOWER ALKYL ESTERS

[75] Inventors: Noboru Uchiyama, Yokkaichi; Masanori Nagao, Kawasaki; Naomasa Mizoguchi, Tokyo, all of Japan

[73] Assignee: Ajinomoto Co., Inc., Tokyo, Japan

[22] Filed: Dec. 20, 1974

[21] Appl. No.: 534,706

[30] Foreign Application Priority Data
July 23, 1974    Japan.............................. 49-84351

[52] U.S. Cl........................................... 260/112.5 R
[51] Int. Cl.[2].................... C07C 103/52; A23L 1/22
[58] Field of Search .............................. 260/112.5 R

[56] References Cited
UNITED STATES PATENTS
3,798,206    3/1974    Uchiyama et al............ 260/112.5 R
3,833,553    9/1974    Ariyoshi et al............... 260/112.5 R

OTHER PUBLICATIONS

Kovacs et al.: *J. Am. Chem. Soc.*, 85, 1839–1844 (1963).

*Primary Examiner*—Lewis Gotts
*Assistant Examiner*—Reginald J. Suyat
*Attorney, Agent, or Firm*—Hans Berman

[57] ABSTRACT

When hydrogen halide salts of L-aspartic anhydride are reacted with lower alkyl esters of L-phenylalanine to produce the corresponding L-aspartyl-L-phenylalanine esters, a significant increase in yield and in the proportion of the α-isomer to the β-isomer is achieved when the reaction is carried out in the presence of a lower alkanol and of a strong acid, such as sulfuric acid, hydrogen chloride, or mono-esters of sulfuric acid with a lower alkanol.

8 Claims, No Drawings

METHOD OF PRODUCING α-L-ASPARTYL-L-PHENYLALANINE LOWER ALKYL ESTERS

This invention relates to α-L-aspartyl-L-phenylalanine lower alkyl esters, and particularly to a method of producing the α-L-aspartyl-L-phenylalanine lower alkyl esters which are known sweetening agents.

These esters were prepared heretofore by reacting esters of L-phenylalanine with a derivative of L-aspartic acid in which the amino group and the β-carboxy group had been masked and the α-carboxy group had been converted to a reactive functional group. After the reaction, the masking groups had to be removed (U.S. Pat. No. 3,475,403). This known method requires many steps and relatively expensive reagents.

L-Aspartyl-L-phenylalanine lower alkyl esters are produced in good yields in a single step by the known reaction of a hydrogen halide salt of L-aspartic anhydride with a lower alkyl ester of L-phenylalanine. The product obtained consists of the desired α-L-aspartyl-L-phenylalanine ester and the bitter-tasting β-isomer.

It has now been found that the overall yield of L-aspartyl-L-phenylalanine esters and the proportion of the α-isomer in the reaction product can be increased significantly when the reaction of a hydrogen halide salt of L-aspartic anhydride with a lower alkyl ester of L-phenylalanine is carried out in the presence of a lower alkanol and of sulfuric acid, hydrogen chloride, or a mono-ester of sulfuric acid with a lower alkanol.

The terms "lower alkyl" and "lower alkanol" in this application refer to compounds having 1 to 4 carbon atoms. The methyl and ethyl esters of α-L-aspartyl-L-phenylalanine and of sulfuric acid are preferred over the propyl and butyl esters, as are methanol and ethanol. The hydrogen halide salts of L-aspartic anhydride referred to in this application are the chloride and bromide.

The reaction is performed in any liquid medium which is substantially inert to the reactants and to the product. The classes of suitable solvents or diluents (and typical representatives of these classes) include water, halogenated hydrocarbons (chloroform, dichloromethane, ethylenedichloride), ethers (tetrahydrofuran, dioxane, diethyl ether), esters (ethyl acetate, methyl propionate, ethyl propionate), hydrocarbons (toluene, xylene, hexane, cyclohexane), nitriles (acetonitrile), amides (dimethylformamide), lactones (γ-butyrolactone), nitrated hydrocarbons (nitromethane) and their mixtures. Obviously, this list is far from complete. The halogenated hydrocarbons such as ethylenedichloride are preferred in the application of this invention on an industrial scale.

The amount of solvent or diluent is not critical and will be chosen so as to make the recovery of the desired product efficient. A homogeneous reaction mixture is preferably prepared for the reaction.

The lower alkanol present in the inert solvent should amount to 2 to 20%, preferably 3 to 15% by volume of the inert solvent. A larger amount of the alcohol reduces the yield of the desired α-isomer.

The reaction temperature is not critical because of the high reactivity of the L-aspartic anhydride salts and the L-phenylalanine esters. The reaction proceeds at ordinary room temperature, and the reaction rate increases with temperature. At temperatures of 60°C or more, the reactants tend to racemize at an undesirable rate. At a reaction temperature below about 10°C, the highest yield of the desired α-isomer is usually obtained. There is no critical lower temperature limit other than that set by solidification of the liquid reaction medium.

The sequence in which the reactants are combined is a matter of choice. It is usually most convenient to dissolve the L-phenylalanine ester in the inert solvent or diluent, to add the strong acid and the alcohol to the solution, and to introduce the L-aspartic anhydride salt last with stirring. However, one may also start from a solution of the L-aspartic anhydride salt in a solvent or diluent, and admix a suspension or dispersion of the L-phenylalanine ester, the strong acid and the alcohol being added to either component prior to mixing.

The L-phenylalanine esters are employed in amounts at least equimolecular to the L-aspartic anhydride salt, and an excess of the ester is preferred. Nothing is gained by employing a very large excess so that the preferred mole ratio of the L-phenylalanine ester to the L-aspartic anhydride salt is between 1:1 and 10:1, especially between 2:1 and 6:1.

When a salt of L-phenylalanine lower alkyl ester with one of the aforementioned strong acids, such as sulfuric acid, hydrogen chloride, monomethylsulfuric acid, or monoethylsulfuric acid is used as a starting material, it may be neutralized with sodium carbonate prior to the reaction, but the salt may also be employed directly to a source of both the L-phenylalanine ester and the strong acid.

When the phenylalanine ester is reacted with the aspartic anhydride salt in an inert solvent in the presence of the strong acid or the alcohol alone, a significant increase in the proportion of the desired α-isomer to the β-isomer is not achieved. The necessary amount of strong acid varies slightly from one acid to the other, but is in the range of 0.05 to 0.5 mole, preferably 0.1 to 0.4 mole per mole of the L-phenylalanine ester. Much more than 0.5 mole of the strong acid reduces the yield of the desired α-isomer.

When the inert solvent or diluent is water-soluble, the reaction mixture is evaporated in a vacuum, the residue is dissolved in water, and the aqueous solution is extracted with a suitable water-insoluble solvent such as ethyl acetate or ethylene dichloride to remove unreacted phenylalanine ester. The L-aspartyl-L-phenylalanine ester is recovered from the extracted aqueous layer by partial evaporation in a vacuum. When the reaction medium is insoluble in water, the reaction mixture is extracted with water at a pH of about 5 to 6, and the dipeptide ester is recovered from the aqueous layer while unreacted phenylalanine ester remains in the organic solvent phase. If water is the solvent or diluent, recovery starts with solvent extraction for removal of the unreacted excess of phenylalanine ester.

The L-aspartyl-L-phenylalanine ester obtained mainly consists of the desired α-isomer which can be purified of the bitter-tasting β-isomer by recrystallization. However, the two isomers differ in so many respects that several other separation methods are practical. The hydrochloride of the α-isomer is so much less soluble in water than that of the β-isomer, that the α-isomer can be precipitated in pure, crystalline form from an aqueous solution of the isomer mixture by the addition of hydrochloric acid. When a mixture of the isomers is treated with acetone or methylethylketone, only the α-isomer goes into solution as a 4-imidazolidinone derivative from which the pure α-isomer can be recovered by hydrolysis. Only the α-isomer forms adducts with cinnamic acid, β-resorcyclic acid, 3,5-dinitrophenol, and gentisic acid in aqueous media, and the adducts are readily decomposed.

The following Examples further illustrate the invention. In these Examples, the indicated yields are based on the aspartic anhydride salt used as a starting material.

EXAMPLE 1

241 g (1.1 Mole) L-phenylalanine methyl ester hydrochloride was dissolved in 900 ml water, and the solution was neutralized with 71 g sodium carbonate. The liberated L-phenylalanine methyl ester was extracted with 2 l ethylene dichloride to give an L-phenylalanine methyl ester solution containing 1.05 mole of the ester. 150 ml Methanol was added to the solution.

After being cooled to −20°C, the solution was mixed with 17.8 ml (0.32 mole) concentrated sulfuric acid. 39 g (0.258 Mole) L-aspartic anhydride hydrochloride was added to the solution, and the resulting mixture was stirred at −20°C for 30 minutes.

The reaction mixture was combined with 2 l hot water, neutralized with sodium carbonate, and then stirred for a while. The water layer was separated from the organic solvent layer, adjusted to a pH of 4.5, and analyzed by amino acid analyzer. The reaction mixture was found to contain α-L-aspartyl-L-phenylalanine methyl ester in a yield of 75.0% and the β-isomer in a yield of 18.5%.

When the procedure was repeated without sulfuric acid, the yields of the α- and β-isomers were 53.6% and 26.0%, respectively.

When the methanol was omitted from the reaction mixture, the respective yields of α- and β-isomers were 47.1% and 38.8%.

EXAMPLE 2

The procedure as in Example 1 was repeated, but the methanol was replaced by 100 ml ethanol.

The reaction mixture contained α-L-aspartyl-L-phenylalanine methyl ester in a yield of 75.7% and the β-isomer in a yield of 18.4%.

EXAMPLE 3

A solution of 1.05 mole L-phenylalanine methyl ester in 2 l ethylene dichloride was prepared as in Example 1.

After being cooled to −20°C, the solution was mixed with a monomethyl sulfuric acid solution prepared by the reaction of sulfuric acid with methanol and consisting of 0.32 mole monomethyl sulfuric acid, 0.04 mole sulfuric acid and 100 ml methanol. 39 g (0.258 Mole) L-aspartic anhydride hydrochloride was added last, and the reaction mixture was stirred at −20°C for 30 minutes.

It was worked up as in Example 1 and found to contain α-L-aspartyl-L-phenylalanine methyl ester in a yield of 74.1% and the β-isomer in a yield of 21.9%.

EXAMPLE 4

The procedure of Example 3 was repeated by the methanol solution of monomethyl sulfuric acid was replaced by a solution consisting of 0.30 mole monoethyl sulfuric acid, 0.03 mole sulfuric acid and 80 ml ethanol.

The reaction mixture contained α-L-aspartyl-L-phenylalanine methyl ester in a yield of 74.4% and the β-isomer in a yield of 21.3%.

EXAMPLE 5

A solution of 0.84 mole L-phenylalanine methyl ester in 1.8 l ethylene dichloride was prepared as in Example 1.

Separately, 42.6 g (0.258 mole) L-phenylalanine and 21.5 ml concentrated sulfuric acid were dissolved in 100 ml methanol. The solution was refluxed to form the monomethyl sulfuric acid salt of L-phenylalanine methyl ester, diluted with ethylene dichloride to a total volume of 200 ml, and added to the L-phenylalanine methyl ester solution.

39 g (0.258 Mole) L-aspartic anhydride hydrochloride was added, and the mixture was stirred at −20°C for 30 minutes. It then contained α-L-aspartyl-L-phenylalanine methyl ester in a yield of 74.6% and the β-isomer in a yield of 21.8%.

EXAMPLE 6

A solution of 0.84 mole L-phenylalanine methyl ester mixed in 2 l ethylene dichloride was prepared as in Example 1. After cooling to −20°C, the solution was mixed with 100 ml methanol and 56.5 g (0.258 mole), L-phenylalanine methyl ester hydrochloride.

39 g (0.258 Mole) L-aspartic anhydride hydrochloride was added, and the resulting solution was stirred at −20°C for 30 minutes. The reaction mixture then contained α-L-aspartyl-L-phenylalanine methyl ester in a yield of 75.9% and the β-isomer in a yield of 19.2%.

EXAMPLE 7

241 g (1.1 Mole) L-phenylalanine methyl ester hydrochloride was dissolved in 900 ml water, and neutralized with 71 g sodium carbonate. The liberated L-phenylalanine methyl ester was extracted with 2.3 l ethyl acetate to give an L-phenylalanine methyl ester solution containing 1.05 mole of the ester which was mixed with 150 ml methanol.

After cooling to −20°C, 17.8 ml (0.32 mole) concentrated sulfuric acid and thereafter 39 g (0.258 mole) L-aspartic anhydride hydrochloride were added, and the resulting solution was stirred at −20°C for 30 minutes.

The reaction mixture was combined with 2 l hot water, neutralized with sodium carbonate, and stirred for a while. The aqueous layer was separated from the organic solvent layer and adjusted to a pH of 4.5. The mixture was analyzed in an amino acid analyzer, and found to contain α-L-aspartyl-L-phenylalanine methyl ester in a yield of 76.2% and the β-isomer in a yield of 14.0%.

When L-aspartic anhydride hydrobromide was substituted in the procedures of Examples 1 to 7 for the hydrochloride in equimolecular amounts, substantially identical results were achieved.

What is claimed is:

1. A method of producing an α-L-aspartyl-L-phenylalanine alkyl ester which comprises reacting the hydrochloride or hydrobromide of L-aspartic anhydride with an alkyl ester of L-phenylalanine in a liquid medium essentially consisting of an alkanol, a strong acid, and a diluent substantially inert to said hydrochloride or hydrobromide, said ester of L-phenylalanine, said alkanol, and said strong acid during said reacting, 1. said strong acid being sulfuric acid, hydrogen chloride, or a monoalkyl ester of sulfuric acid in an amount of 0.05 to 0.5 mole per mole of said ester of L-phenylalanine, 2. the mole ratio of said hydrochloride or hydrobromide to said ester of phenylalanine being between 1:1 and 1:10,
  3. the amount of said alkanol being 2 to 20 percent of the volume of said diluent,
  4. said alkyl, said alkanol, and said monoalkyl having not more than four carbon atoms.

2. A method as set forth in claim 1, wherein the temperature of said medium during said reacting is lower than 60°C.

3. A method as set forth in claim 2, wherein said inert solvent is ethylene dichloride.

4. A method as set forth in claim 2, wherein said alkyl, said alkanol, and said monoalkyl have not more than two carbon atoms.

5. A method as set forth in claim 4, wherein the temperature of said medium during said reacting is below 10°C.

6. A method as set forth in claim 5, wherein said amount of said strong acid is 0.1 to 0.4 mole per mole of said ester of L-phenylalanine, the mole ratio of said hydrochloride or hydrobromide to said ester of phenylalanine is between 1:2 and 1:6, and the amount of said alkanol is between 3% and 15% of the volume of said diluent.

7. A method as set forth in claim 1, wherein said strong acid is hydrogen chloride.

8. A method as set forth in claim 1, wherein said strong acid is sulfuric acid.

* * * * *